United States Patent [19]

Yamada et al.

[11] Patent Number: 4,722,779

[45] Date of Patent: Feb. 2, 1988

[54] AIR/FUEL RATIO SENSOR

[75] Inventors: Tetsusyo Yamada; Nobuhiro Hayakawa; Kazunori Yokota; Keiichi Hayashi, all of Aichi; Toyohei Nakajima; Yasushi Okada, both of Saitama, all of Japan

[73] Assignees: NGK Spark Plug Co., Ltd.; Honda Giken Kogyo Kabushiki Kaisha, both of Japan

[21] Appl. No.: 12,467

[22] Filed: Feb. 9, 1987

[30] Foreign Application Priority Data

Feb. 7, 1986 [JP] Japan .................................. 61-26258

[51] Int. Cl.$^4$ ........................................... G01N 27/58
[52] U.S. Cl. .................... 204/410; 204/406; 204/412; 204/425; 204/426
[58] Field of Search ............... 204/410, 412, 425, 426, 204/406, 1 S; 123/489; 60/276

[56] References Cited

U.S. PATENT DOCUMENTS 4,578,171  3/1986  Yamada et al. ..................... 204/406
4,594,139  6/1986  Asayama et al. ................... 204/410

Primary Examiner—G. L. Kaplan
Attorney, Agent, or Firm—Sughrue, Mion, Zinn, Macpeak, and Seas

[57] ABSTRACT

An air/fuel ratio sensor having two units of probe is disclosed each of which comprises two sensing elements, each having a pair of porous electrodes on oppostie sides of an oxygen ion-conductive solid electrolyte; a gas compartment which is formed in contact with one porous electrode for each sensing element and which communicates with the gaseous atmosphere of interest by way of a gas diffusion limiting portion; and an internal reference oxygen source which is formed in contact with one sensing element on the porous electrode side which is opposite the side where said gas compartment is provided. The oxygen source communicates with the outside by way of a leakage resisting portion. The gas compartment in the first unit of probe communicates directly with the gaseous atmosphere of interest by way of a first gas diffusion limiting portion while the gas compartment in the second unit of probe communicates with the gas in the first unit of probe by way of a second gas diffusion limiting portion.

3 Claims, 11 Drawing Figures

AIR/FUEL RATIO SENSOR

BACKGROUND OF THE INVENTION

The present invention relates to an air/fuel (A/F) ratio sensor which detects the A/F ratio of the feed to an internal combustion engine and other combustors on the basis of the concentration of oxygen in the exhaust from such combustors.

Various A/F ratio detectors are used to detect the A/F ratio of an air-fuel mixture feed into internal combustion engines and other combustors on the basis of the concentration of oxygen in the exhaust gas. The device shown in Unexamined Published Japanese patent application No. 178354/1984 comprises two elements each having porous electrodes formed on opposite sides of a tabular oxygen ion-conductive solid electrolyte and which are spaced from each other in a face-to-face relationship by a gas compartment, or the gap where the diffusion of the exhaust gas is limited; one of the elements is used as an oxygen pump for pumping oxygen out of the gap between the two elements, and the other element is used as an oxygen concentration electrochemical cell which produces a voltage in accordance with the difference in oxygen concentration between said gap and the ambient gas atmosphere to be analyzed. This device is so designed that it is capable of detecting an A/F ratio associated signal at least in the fuel-lean region.

It has, however, been found that this type of A/F ratio sensor, which is principally designed to issue a signal in the fuel-lean region where the exhaust gas contains a large amount of residual oxygen, produces a similar signal in the fuel-rich region where the exhaust gas contains a very small amount of residual oxygen because it reacts with other chemical species in the exhaust gas, such as CO, $CO_2$ and $H_2O$. In other words, one signal from the A/F ratio sensor is associated with two different values of A/F ratio. Therefore, this A/F ratio sensor cannot be used for the purposes of A/F ratio control unless it is known definitely whether the combustor is operating in the fuel-lean or fuel-rich region.

According to one method that has been proposed for meeting this need, the atmospheric air is introduced such that it contacts the side of the oxygen concentration electrochemical cell which does not face the oxygen pump element, thereby preventing a detected signal from being inverted in the vicinity of the stoichiometric value of A/F ratio. However, in order to introduce the atmospheric air such that it contacts one side of the oxygen concentration electrochemical cell, the A/F ratio sensor must be open to the air and this in turn requires rendering the sensor waterproof by employing a complicated construction.

In order to eliminate this problem, one modification has recently been proposed; according to this proposal, instead of introducing the atmospheric air into the sensor, oxygen is generated at an internal reference oxygen source provided on one side of the oxygen concentration electrochemical cell element, and part of the evolved oxygen is caused to leak into the ambient exhaust gas or into the gas compartment through a leakage resisting portion so that the oxygen partial pressure in the internal reference oxygen source is maintained constant, thereby obviating the need for providing the atmospheric reference (see Japanese patent application Nos. 137586/1985 and 214004/1985).

When a predetermined amount of current is permitted to flow into the oxygen concentration electrochemical cell element of the A/F ratio sensor of the type described above, the oxygen in the gas compartment flows into the internal reference oxygen source and part of the oxygen inflow leaks to the outside through the leakage resisting portion so as to maintain a constant level of oxygen partial pressure in the internal reference oxygen source. This provides the results which are the same as those obtained by introducing the atmospheric air into the sensor and precise A/F ratio detection can be achieved without introduction of the atmospheric air.

Therefore, the A/F ratio sensor described in Japanese patent application Nos. 137586/1985 and 214004/1985 enables the concentration of oxygen in the exhaust gas to be detected as precisely as when the atmospheric air is introduced into the sensor. However, this sensor has detection characteristics which may be depicted as shown in FIG. 10 and the gradient differs so greatly between the fuel-lean and fuel-rich regions of A/F ratio that the precision of detection in the fuel-lean region is not as high as in the fuel-rich region. FIG. 10 depicts the change in pump current, Ip, which occurs when Ip flowing through the oxygen pump element is controlled such that a constant voltage will develop across the oxygen concentration electrochemical cell element. As shown in FIG. 10, the gradient of Ip in the fuel-rich region is about three times as large as the gradient in the fuel-lean region and this contributes to a reduced precision of detection in the fuel-lean region.

The above-described problem is due to the fact that non-oxygen gases such as CO and $H_2$ have higher rates of diffusion than oxygen gas. Stated more specifically, in the fuel-rich region where a relatively small amount of oxygen is present in the exhaust gas, the sensor is so operated that the oxygen partial pressure in the gas compartment is held constant by means of the oxygen pump element which reacts with CO, $CO_2$, $H_2O$ and other oxygen-containing components in the exhaust gas to produce oxygen which then is pumped into the gas compartment. However, in the gas compartment, $H_2$, CO and other rapidly diffusing gases will react with the oxygen that has been pumped into that compartment and the oxygen partial pressure in it will become lowered. In order to compensate for this pressure drop, the oxygen pump element is required to pump in a correspondingly larger amount of oxygen and this leads to an increased amount of pump current which flows through the pump element.

Also, the above-described sensor suffers from another problem. Namely, when it is used in exhaust gas of a motor vehicle, a deposit is adhered onto the gas diffusion limiting portion, resulting in clogging or plugging. This would lead to a defect such that there is an error in an output value representative of the time-basis change in gas diffusion control, i.e., the air/fuel ratio.

SUMMARY OF THE INVENTION

An object, therefore, of the present invention is to provide an A/F ratio sensor that achieves precise A/F ratio detection without introducing the atmospheric air and which, in addition, offers detection characteristics that exhibit high precision not only in the fuel-rich region but also in the fuel-lean region.

Another object of the invention is an A/F ratio sensor having a self-compensating function for the output time-basis change.

In order to attain this object, the A/F ratio sensor of the present invention employs two units of probe, each consisting of:

two sensing elements each having a pair of porous electrodes on opposite sides of an oxygen ion-conductive solid electrolyte;

a gas compartment which is formed in contact with one porous electrode for each sensing element and which communicates with the gaseous atmosphere of interest by way of a gas diffusion limiting portion; and an internal reference oxygen source which is formed in contact with one sensing element on the porous electrode side which is opposite the side where said gas compartment is provided, said oxygen source communicating with the outside by way of a leakage resisting portion.

The A/F ratio sensor having this construction is further characterized in that the gas compartment in the first unit of probe communicates directly with the gaseous atmosphere of interest by way of a first gas diffusion limiting portion and that the gas compartment in the second unit of probe communicates with the gas compartment in said first unit of probe by way of a second gas diffusion limiting portion.

DETAILED DESCRIPTION OF THE INVENTION

Figure 1:
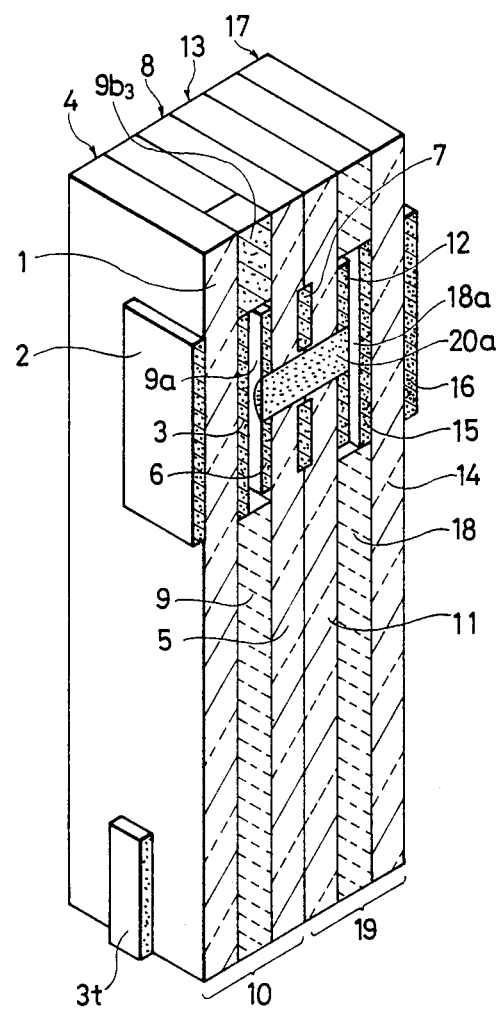
FIG. 1 is a partial fragmentary perspective view illustrating the A/F ratio sensor of the present invention according to one embodiment thereof.

Typical examples of the oxygen ion-conduvtive solid electrolyte used in each of the two sensing elements are a solid solution of zirconia and yttria, as well as a solid solution of zirconia and calcia. Other usable materials include: solid sollutions of cerium dioxide, thorium dioxide and hafnium dioxide; a solid solution of the perovskite type oxide; and a solid solution of a trivalent metal oxide. The porous electrodes formed on opposite sides of these solid electrolytes may be formed of platinum, rhodium or other metals which catalyze oxidative reaction. These electrodes may be formed by various methods; in one method, a paste based on a powder of platinum, rhodium or any other appropriate metal which is mixed with a powder of the same ceramic material as the solid electrolyte is printed in a predetermined pattern on the solid electrolyte by a thick-film deposition technique, followed by sintering of the printed coat; in another mehtod, the powder of the startin material is applied onto the solid electrolyte by a suitable thin-film deposition technique such as flame spraying, chemical plating or evaporation. Those electrodes which are to be directly exposed to the exhaust gas and the electrodes on the gas compartment side are preferably coated with a porous protective layer of alumina, spinel, zirconia, mullite or the like which is formed by a thick-film deposition technique.

The gas compartment provides the space into which the ambient exhaust gas is introduced in a diffusion-limiting manner through the gas diffusion limiting portion which is intended to limit the diffusion of the gas to be analyzed, or the exhaust gas. This compartment may be formed by inserting a hollow spacer made of $Al_2O_3$, spinel, forsterite, steatite, zirconia or the like between two sensing elements, the gas diffusion limiting portion being provided in the form of an aperture that is made in one or more areas in the spacer and which establishes communication between the ambient gaseous atmosphere of interest and the gas compartment. The gas diffusion limiting portion is not limited to any particular shape so long as it is capable of establishing communication between the ambient exhaust gas and the gas compartment in a diffusion-limiting manner; for instance, the spacer may be partly or entirely replaced by a porous body or, alternatively, apertures may be provided in the spacer (including a thick coat). If desired, the spacer may be provided only in the area between the terminal sides of the two sensing elements, thereby forming a gap between these sensing elements which serves as a gas diffusion limiting gap that is integral with the gas compartment. The gas compartment may be entirely filled with a porous material which is desirably an electrical insulator.

The internal reference oxygen source serves as a collector of the oxygen which has moved from the gas compartment by means of the current flowing through the sensing element that is in contact with said oxygen source. The oxygen source may be formed by laminating said sensing element with a shield plate that is made of $Al_2O_3$, spinel, forsterite, steatite, zirconia or the like and which has a recess matching the shape of the electrode formed on the side of said sensing element which is opposite the gas compartment side. The internal reference oxygen source communicates with the gas compartment by way of the leakage resiting portion so as to permit the leakage of the internal oxygen toward the gas compartment side. This leakage resisting portion may be formed by providing a porous layer between the internal reference oxygen source and a through-hole made in the sensing element to establish communication between the latter and the gas compartment.

It suffices that the leakage resisting portion enables the oxygen in the internal reference oxygen source to be gradually moved into the gas compartment or to the outside (e.g., the ambient gas to be analyzed) and, therefore, communication may be established between the internal reference oxygen source and the gas compartment or the ambient gas of interest by means of tiny holes. If desired, instead of using a shield plate having a recess as the internal reference oxygen source, a flat (unrecessed) shield plate may be directly formed on the pertinent sensing element and, in this case, the communicating pores initially present in the porous electrode on that sensing element will serve as the internal reference oxygen source.

One important feature of the A/F ratio sensor of the present invention is that it employs two units of probe each consisting of two sensing elements, a gas compartment and an internal reference oxygen source in the manner described in the foregoing pages. As already mentioned, the rates of diffusion of gaseous components in the exhaust in the fuel-lean region differ from those in the fuel-rich region and an A/F ratio sensor employing only one unit of probe is unable to achieve as good precision of detection in the fuel-lean region as in the fuel-rich region. In order to solve this problem, the sensor of the present invention employes an integral combination of two units of probe that provide different diffusion rates; the first probe which achieves a faster diffusion rate is used to detect a value of A/F ratio in the fuel-lean region and the second probe achieving a slower diffusion rate is used to detect a value of A/F ratio in the fuel-rich region. By employing these two units of probe in combination, the sensor of the present provides detection characteristics wherein the sensitivity changes continuously over the full operating range including the fuel-lean and the fuel-rich region.

To state the feature of the sensor of the present invention more specifically, it is so constructed that the exhaust gas is directly introduced into the gas compartment in the first unit of probe through the first gas diffusion limiting portion whereas the exhaust gas in the gas compartment in the first unit of probe is introduced into the gas compartment in the second unit of probe through the second gas diffusion limiting portion. By employing this construction, the detection characteristics for the fuel-lean region which are obtained in the first unit of probe can be rendered comparable to those for the fuel-rich region which are obtained in the second unit of probe. In this connection, it should be mentioned that in view of the gradient of the characteristic curve in the fuel-rich region which is approximately three times as large as in the fuel-lean region, the second gas diffusion limiting portion preferably has a resistance to gas diffusion that is at least twice the value offered by the first gas diffusion limiting portion.

The two units of probe may be assembled into an integral form by joining directly the two shield plates, one covering the internal reference oxygen source in the first unit of probe while the other covers the oxygen source in the second unit of probe, in such a manner that the gas compartment in the second unit of probe will communicate with the gas compartment in the first unit of probe by way of the gas diffusion limiting portions in the respective units of probe. As already mentioned, the internal reference oxygen source may be provided by the communicating pores present in a porous electrode on each sensing element and, in this case, one oxygen source, rather than two, will suffice if one electrode is commonly used for the two sensing elements. If only one internal reference oxygen source is used, two leakage resisting portions may be provided such that the oxygen in that source will leak into the gas compartment in each unit of probe. Alternatively, in view of the fact that the two gas compartments communicate with each other, only one leakage resisting portion that communicates with either one of the gas compartments may be provided so that oxygen will leak solely into that gas compartment. It should also be noted that the leakage resisting portion may be formed to have direct communication with the ambient gaseous atmosphere of interest.

The A/F ratio sensor of the present invention having the construction described above may be operated in such a manner that the sensing element in each unit of probe that is in contact with the internal reference oxygen source acts as an oxygen generating and oxygen concentration electrochemical cell while the other sensing element works as an oxygen pump. Stated more specifically, a constant current is allowed to flow through the sensing element (i.e., oxygen concentration electrochemical cell) that is in contact with the internal reference oxygen source by applying a voltage between the electrodes on opposite ends of this sensing element; as a result, the oxygen in the gas compartment is pumped into the internal reference oxygen source and, at the same time, a voltage will develop that is proportional to the oxygen partial pressure in the gas compartment which is referenced against the oxygen partial pressure in the internal reference oxygen source that has been generated by the pumping of oxygen into that oxygen source. The voltage generation at the oxygen concentration electrochemical cell can be controlled by the other sensing element (i.e., oxygen pump) which, in response to the didirectional current flow that is produced by application of a predetermined voltage between the electrodes on opposite sides of that sensing element, will pump out oxygen from the gas compartment into the ambient exhaust gas or pump oxygen from the exhaust gas into the gas compartment. Using these operating principles, A/F ratio detection, or the detection of the concentration of oxygen in the exhaust gas, may be accomplished as follows: a given voltage is applied to the oxygen concentration electrochemical cell through a resistor; the current flowing through the oxygen pump is so controlled that a constant voltage will develop across the resistor; and the resulting control current is picked up as an output which is indicative of the A/F ratio of the exhaust gas. Alternatively, a constant current is caused to flow through the oxygen pump by pumping a predetermined amount of oxygen out of or into the gas compartment, and the resulting voltage which develops across the oxygen concentration electrochemical cell is picked up as a signal that is indicative of the A/F ratio of the exhaust gas. In either method of A/F ratio detection, the oxygen concentration electrochemical cell has to be fed with a constant or almost constant current so that the oxygen partial pressure in the internal reference oxygen source will be held constant or substantially constant.

As already mentioned, the A/F ratio sensor of the present invention is so constructed that the exhaust gas which has been fed into the gas compartment in the first unit of probe will be introduced into the gas compartment in the second unit of probe through the second gas diffusion limiting portion. This is effective in retarding the gas diffusion through the second unit of probe as compared with the diffusion through the first unit of probe, and the rates of diffusion of $H_2$, CO and other rapidly diffusing components in the exhaust gas that is introduced into the second unit of probe when the A/F ratio to be detected is in the fuel-rich region can be approximated by the rate of diffusion of oxygen in the exhaust gas that is introduced into the first unit of probe when the A/F ratio is in the fuel-lean region. Consequently, by operating the sensor of the present invention in such a manner that values of A/F ratio in the fuel-lean region are detected with the first unit of probe while those in the fuel-rich region are detected with the second unit of probe, approximately equal levels of detection sensitivity and precision can be attained over the full range of A/F ratio.

Figure 2:
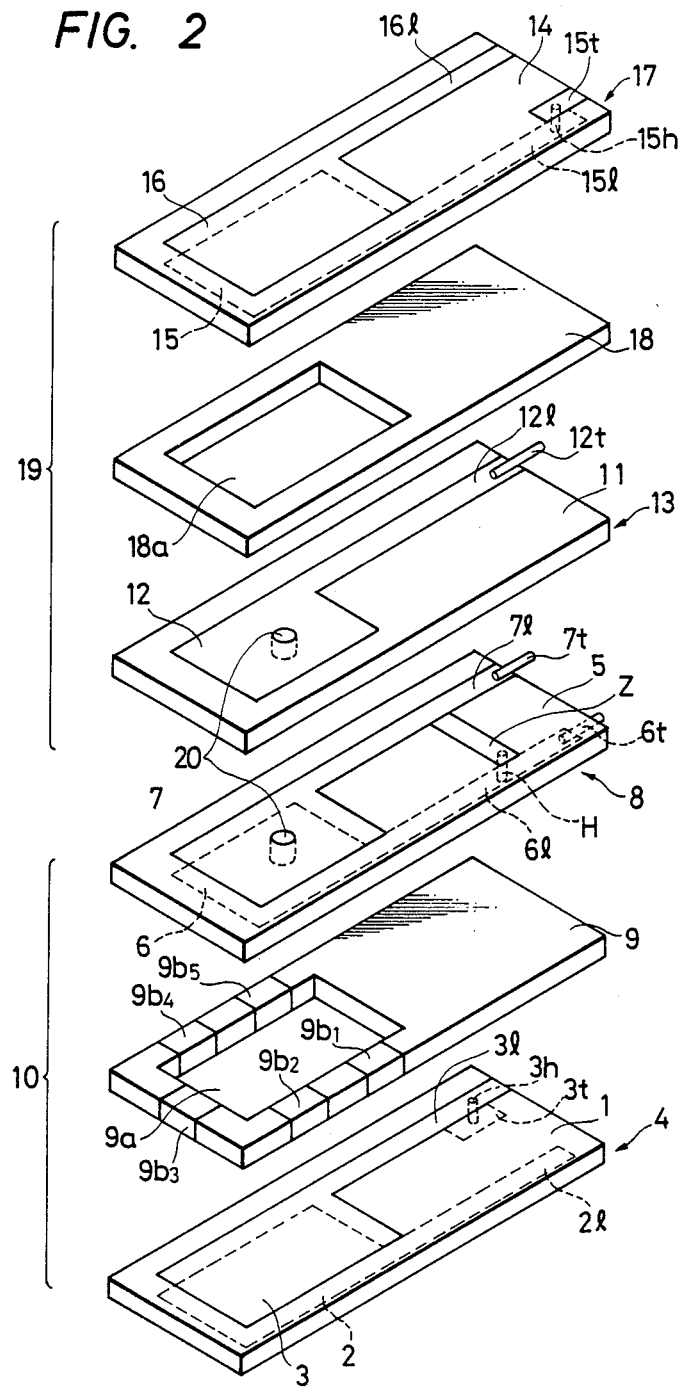
FIG. 2 is a perspective view showing the sensor of FIG. 1 in an unassembled form.

A first embodiment of the A/F ratio sensor of the present invention is hereinafter described with reference to the accompanying drawings. First, the general layout of the sensor of the first embodiment is shown in FIGS. 1 and 2; FIG. 1 is a partial fragmetary perspective view of the sensor and FIG. 2 shows it in an unassembled form.

As shown, the A/F ratio sensor of the present invention is composed of two units of probe, 10 and 19. The first unit of probe 10 consists of: an oxygen pump element 4 having porous electrodes 2 and 3 formed on opposite sides of a solid electrolyte plate 1; an oxygen concentration electrochemical cell element 8 having porous electrodes 6 and 7 formed on oppposite sides of a solid electrolyte plate 5; and a spacer 9 that is sandwiched between these two sensing elements 4 and 8 and which has a hollow portion 9a defined by the two opposing porous electrodes 3 and 6 formed on the elements 4 and 8, respectively. The second unit of probe 19 consists of: an oxygen concentration electrochemical cell element 13 having porous electrodes 7 and 12 formed on opposite sides of a solid electrolyte plate 11; an oxygen pump element 17 having porous electrodes 15 and 16 formed on opposite sides of a solid electrolyte plate 14; and a spacer 18 that is sandwiched between these two sensing elements 13 and 17 and which has a hollow portion 18a defined by the two opposing porous electrodes 12 and 15 formed on the sensing elements 13 and 17, respectively.

The spacer 9 in the first unit of probe 10 is provided to form a gas compartment between the porous electrodes 3 and 6 wherein gas diffusion is limited. The gas compartment is provided by the hollow portion 9a. In the embodiment shown, gas diffusion limiting portions, 9b1 to 9b5, that are made of porous alumina and which serve as the first gas diffusion limiting portion are provided at five locations around the hollow portion 9a so as to permit the ambient gas of interest to be introduced into the hollow portion 9a.

Like the spacer 9, the spacer 18 in the second unit of probe 19 is provided to form a gas compartment between the porous electrodes 12 and 15, and the gas compartment is provided by the hollow portion 18a. The gas to be analyzed is introduced into the hollow portion 18a through the gas diffusion limiting portions, 9b1 to 9b5, and the gas compartment (hollow portion 9a) in the first unit of probe, and through communicating holes 20 that are formed in the porous electrodes 6, 7 and 12 and in the solid electrolyte plates 5 and 11 so that they will communicate with the hollow portion 9a. The communicating holes 20 correspond to the second gas diffusion limiting portion and in the embodiment shown they are filled with a porous material 20a such as alumina.

In the illustrated A/F ratio sensor, the porous electrode 7 is commonly used for both the oxygen concentration electrochemical cell element 8 in the first unit of probe 10 and the oxygen concentration electrochemical cell element 13 in the second unit of probe 19. This porous electrode 7 is also used as an internal reference oxygen source for the two probes 10 and 19 in which oxygen is generated in response to a predetermined current that is supplied to the oxygen concentration electrochemical cell elements 8 and/or 13. In order for the generated oxygen to leak into the hollow portion 9a which serves as the gas compartment in the first unit of probe 10, the lead 7l on the porous electrode 7 is connected to the lead 6l on the porous electrode 6 both by a porous insulator Z which is typically made of alumina and by a through-hole H. In other words, the porous insulator Z, through-hole H, and the leads 7l and 6l provide leakage resisting portions and, as already mentioned, the oxygen generated in the porous electrode 7l serving as the internal reference oxygen source is permitted to leak into the gas compartment in the first unit of probe 10 through these leakage resisting portions.

The porous electrodes 2, 3, 15 and 16 for the oxygen pump elements 4 and 17 have their terminal ends formed on the outer surface of the wall of the A/F ratio sensor. Since the porous electrodes 2 and 16 are formed to be exposed externally, their respective leads 2l and 16l are directly used as their terminals. Terminals for the porous electrodes 3 and 15 which are embedded in the sensor are provided by electrically connecting their leads 3l and 15l to terminals 3t and 15t on the outer surfaces of the solid electrolyte plates 1 and 14 by through-holes 3h and 15h, respectively. Terminals for the porous electrodes 6, 7 and 12 on the oxygen concentration electrochemical cell elements 8 and 13 are provided in the form of externally projecting lead wires 6t, 7t and 12t which are connected to their respective leads 6l, 7l and 12l.

Figure 3:
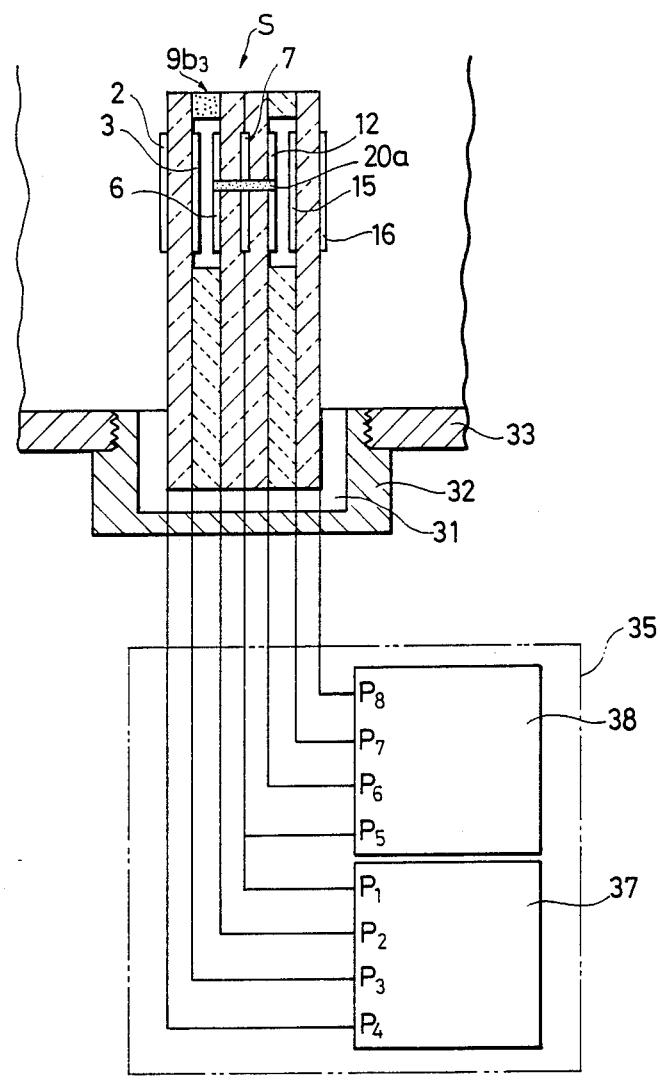
FIG. 3 is a cross-sectional view showing how the A/F ratio sensor of FIG. 1 is mounted on an exhaust pipe.

As shown in FIG. 3, the A/F ratio sensor according to the embodiment illustrated above is typically enclosed to prevent oxygen from leaking to the outside of the porous electrode 7 and is mounted on the exhaust pipe 33 in an internal combustion engine by means of a fixing member 31 and a threaded member 32. Being installed in this manner, the sensor S is used to detect the A/F ratio of the air/fuel mixture feed to the engine on the basis of the measured value of the concentration of oxygen in the exhaust gas. Therefore, in order to determine the detection characteristics of the sensor S experimentally, the present inventors mounted the sensor on the exhaust pipe 33 in an internal combustion engine in the manner shown in FIG. 3 and operated it by means of an A/F ratio detector circuit 35. The experiment conducted for this purpose is hereunder described. For the sake of clarity, the A/F ratio sensor S mounted on the exhaust pipe is shown in FIG. 3 with the lead and terminals for the individual porous electrodes being omitted.

The A/F ratio detector circuit 35 includes detectors 37 and 38 that are to be used in association with the first and second units of probe 10 and 19, respectively. The detector 37 (or 38) is so constructed that when a current is caused to flow through the oxygen concentration electrochemical cell element 8 (or 13) in the probe 10 (or 19), oxygen is generated in the porous electrode 7 serving as the internal reference oxygen source, and that the current flowing through the oxygen pump element 4 (or 14) is controlled bidirectionally such that the voltage which develops across the oxygen concentration electrochemical cell element 8 (13) in proportion to the ratio of the oxygen partial pressure in the hollow portion 9a (or 18a), which serves as the gas compartment, to the oxygen partial pressure in the porous electrode 7, namely, the oxygen partial pressure in the hollow portion 9a (or 18a), will be held constant, with the so controlled current being picked up as an output detection signal.

Figure 4:
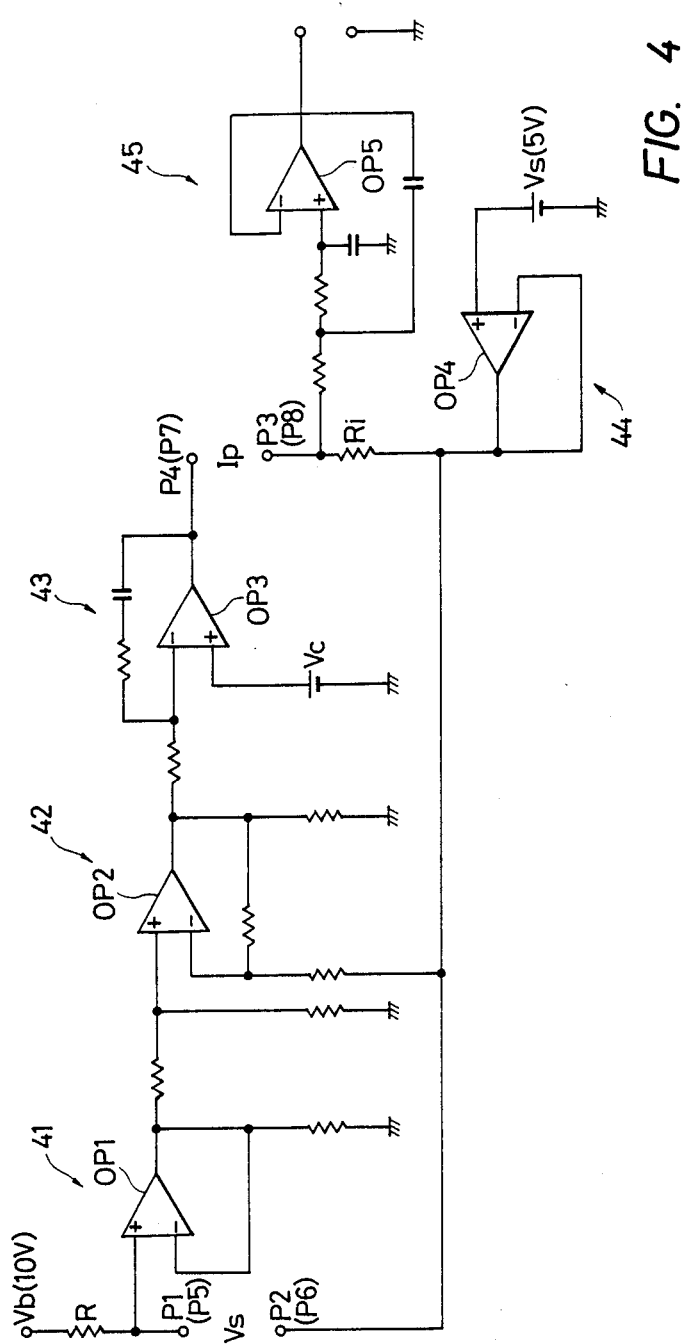
FIG. 4 is an electrical circuit diagram showing a detection circuit that is employed to determine the detection characteristics of the individual probe units provided in the A/F ratio sensor.
Figure 5:
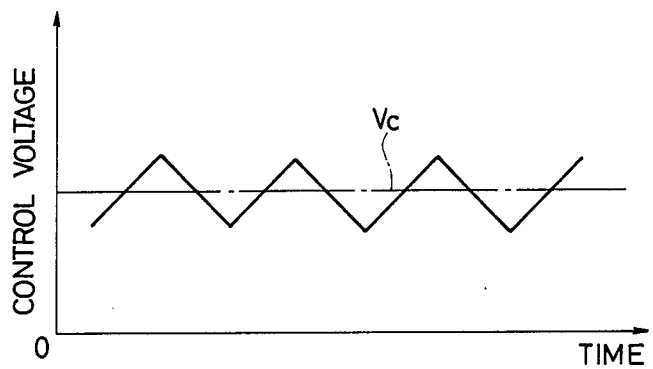
FIG. 5 is a diagram showing the control signal for the oxygen pump element that is generated in the detector circuit of FIG. 4.

The circuit configuration of the detector 37 (or 38) is shown in FIG. 4; it consists of a resistor R through which a predetermined voltage, Vb (10 volts) is applied to the porous electrode 7 on the oxygen concentration electrochemical cell element 8 (or 13) and which will limit the current flowing through the other porous electrode 6 (or 12) which is supplied with a reference voltage, Vs (5 volts); a buffer circuit 41 that is composed of an operational amplifier OP1 for detecting the voltage that has developed across the oxygen concentration electrochemical cell element 8 (or 13) and which has been boosted by the reference voltage, Vs; a non-inverting amplifier circuit 42 that is composed of an operational amplifier OP2 for amplifying the detection voltage produced as an output from the buffer circuit 41; a comparator/integrator circuit 43 that is composed of an operational amplifier OP3 which compares the amplified detection voltage with the predetermined reference voltage Vc and produces an output control voltage having the waveform shown in FIG. 5 which gradually decreases at a predetermined integration constant when the amplified detection voltage is greater than the reference voltage Vc and increases gradually at the same constant for integration when the detection voltage is smaller than Vc; a buffer circuit 44 that is composed of an operational amplifier OP4 for producing the reference voltage Vs as an output; a current detecting resistor Ri through which Vs from the buffer circuit 44 is applied to the porous electrode 3 (or 15) on the hollow portion 9a (or 18a) side of the oxygen pump element 4 (or 17) and which serves to detect the current flowing between the electrode 3 (or 15) and the other porous electrode 2 (or 16) which has been supplied with the control voltage from the comparator/integrator circuit 43; and an output circuit 45 that is composed of an operational amplifier OP5 from which the voltage developing in the resistor Ri is produced as an output detection signal.

The detector circuit having the configuration described above was used to operate the two units of probe 10 and 19 independently of each other, and the resulting detection signals were used as a basis for calculating the values of pump current Ip which had flowed through the oxygen pump elements 4 and 17. The results of calculation are shown graphically in the diagram of FIG. 6, in which the dashed line indicates the results from the first unit of probe 10 and the one-short-and-one-long dashed line represents the results from the second unit of probe 19. The specifications of the major components of the A/F ratio sensor employed in this experiment are shown in the following table.

TABLE

| Component | Dimensions (T × W × L) | Principal ingredient |
|---|---|---|
| Solid electrolyte plates (1, 5, 11, 14) | 0.5 mm × 4 mm × 45 mm | Zirconia |
| Porous electrodes (2, 3, 15, 16) | 30 um × 2.4 mm × 5.8 mm | Platinum |
| Porous electrodes (6, 7, 12) | 30 um × 2.4 mm × 5.8 mm | Platinum |

TABLE-continued

| Component | Dimensions (T × W × L) | Principal ingredient |
|---|---|---|
| Spacers (9, 18) | 60 um × 4 mm × 45 mm | Alumina |
| Hollow portions or gas compartments (9a, 18a) | 60 um × 2.4 mm × 7.2 mm | — |
| Gas diffusion limiting portions (9b1–9b5) | 1.7 mm wide | Porous alumina |
| Communicating hole (20) | 0.58 mm$^\phi$ (filled with porous material 20a) | (Porous material 20a was alumina) |

Figure 6:
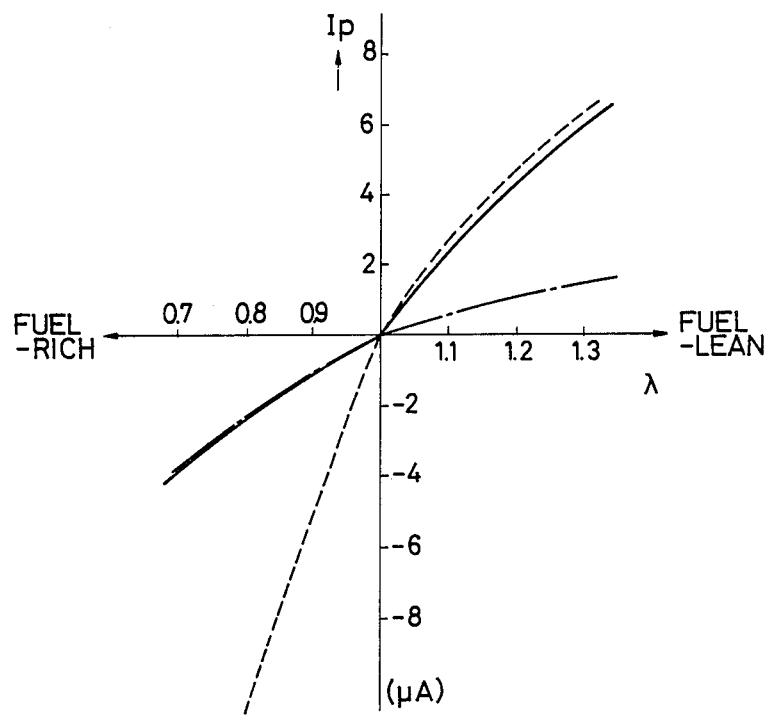
FIG. 6 is a diagram showing the detection results that may be obtained with this circuit.

As shown in FIG. 6, the pump current Ip obtained from the first unit of probe 10 has a larger gradient than Ip obtained from the second unit of probe 19. The reason for this difference in gradient is as follows: the hollow portion 9a, or the gas compartment, in the first unit of probe 10 is directly supplied with the gas of interest through the surrounding gas diffusion limiting portions 9b1 to 9b5, whereas the hollow portion 18a, or the gas compartment, in the second unit of probe 19 is supplied with the gas of interest first through the gas diffusion limiting portions 9b1 to 9b5, then through the hollow portion 9a and the communicating holes 20 filled with the porous material 20a, and the gas of interest will diffuse through the second unit of probe 19 at a sufficiently retarded rate to require a correspondingly smaller amount of pump current.

The experimental results depicted in FIG. 6 show that if A/F ratio detection for the fuel-lean region is effected with the first unit of probe 10 while the second unit of probe 19 is used to perform detection in the fuel-rich region, two curves of detection characteristics having similar gradients are attained from the fuel-rich and fuel-lean regions of A/F ratio, thereby providing constant precision of detection for both the lean and rich regions. To state this more specifically, the A/F ratio sensor S of the illustrated embodiment may be operated to achieve A/F ratio detection by means of a detector circuit which provides automatic switching between the operation of the first unit of probe 10 for detection in the fuel-lean region and the operation of the second unit of probe 19 for detection in the fuel-rich region, and this system offers an effective solution to the problem associated with the prior art system, that is, the sensitivity of detection in the fuel-lean region is too much lower than in the fuel-rich region to ensure reliable A/F ratio control. In the pages that follow, an example of the use of the A/F ratio sensor S is described with reference to the case where it is used in association with a detector circuit that provides switching between the fuel-lean and fuel-rich regions for the operation of the two units of probe and which produces the results of detection that are shown by the solid line in FIG. 6.

Figure 7:
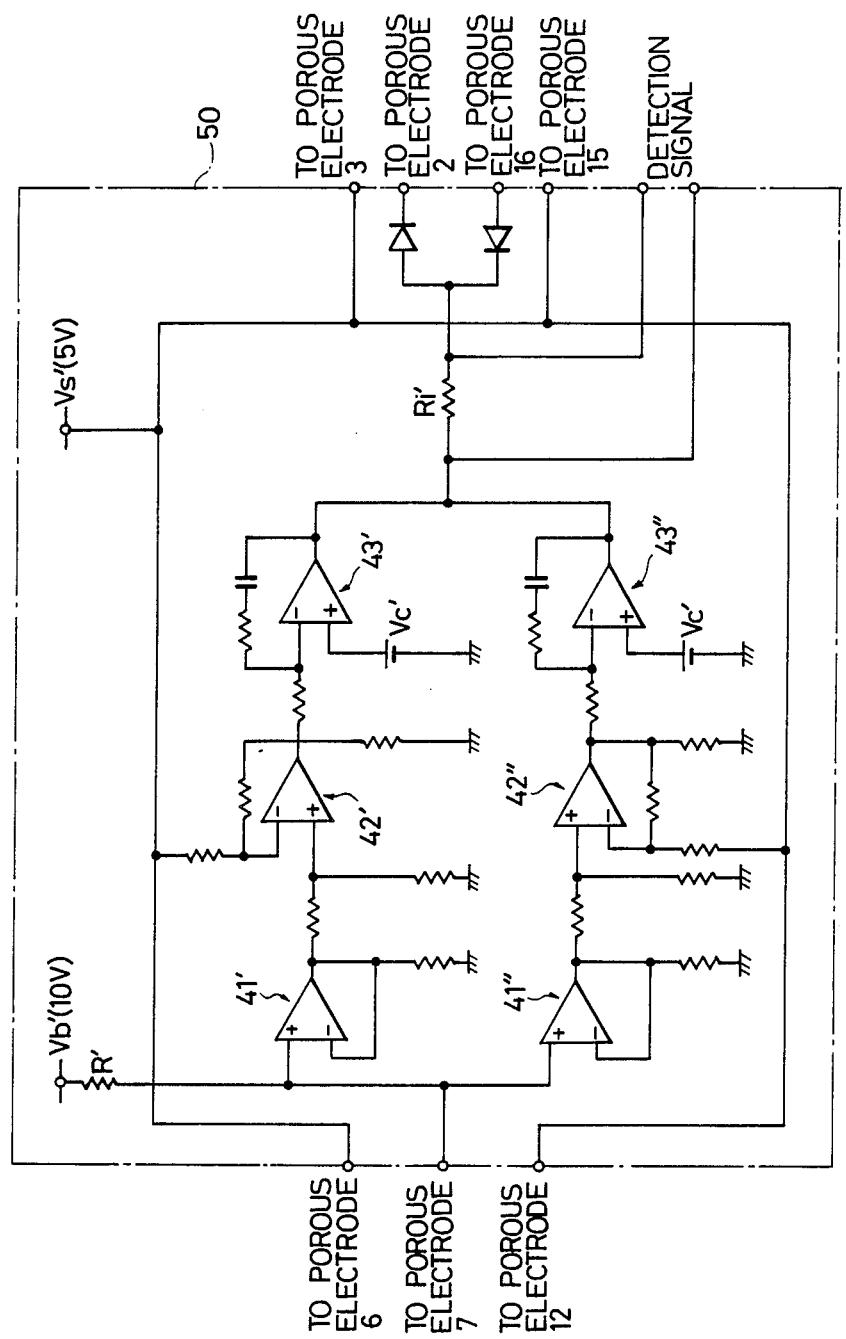
FIG. 7 is an electrical circuit diagram showing an A/F ratio detector circuit that may be advantageously used to achieve A/F ratio detection with the sensor of the first embodiment of the present invention.

The detector circuit indicated at 50 in FIG. 7 includes two detectors which, like the detectors 37 and 38 shown in FIG. 4, are associated with the probes 10 and 19, respectively, and consist individually of buffer circuits 41' and 41", non-inverting amplifier circuits 42' and 42", comparator/integrator circuits 43' and 43", and a resistor R' through which a predetermined voltage Vb' is applied to the porous electrode 7 and which will limit the current flowing through the oxygen concentration electrochemical cell elements 8 and 13. In addition to these components, the detector circuit 50 includes diodes D1 and D2, as well as a current detecting resistor Ri'. By means of the diode D1, the direction of the pump current flowing through the oxygen pump element 4 which is controlled to develop a constant voltage across the associated oxygen concentration electrochemical cell element is limited in such a manner that oxygen will be pumped out of the hollow portion 9a in the first unit of probe 10; and by means of the diode D2, the direction of the pump current flowing through the oxygen pump element 17 which is also controlled to develop a constant voltage across the associated oxygen concentration electrochemical cell element is limited in such a manner that oxygen will be pumped into the hollow portion 18a in the second unit of probe 19. The resistor Ri' then detects the sum of the two pump currents whose direction has been restricted by these diodes D1 and D2.

When the A/F ratio to be detected is within the fuel-lean region, the detector circuit 50 described above will produce as an output detection signal the pump current that is obtained from the first unit of probe 10; on the other hand, when the A/F ratio to be detected is within the fuel-rich region, the circuit 50 will produce the pump current from the second unit of probe 19 as an output detection signal. As a result, the operator has no need to effect manual switching from one unit of probe to the other in accordance with the A/F ratio to be detected. The detection achieved by the circuit 50 was found to provide the characteristic curve shown by the solid line in FIG. 6.

As already shown in FIG. 6, the A/F ratio sensor according to the illustrated embodiment produces two detection signals when the first and second units of probe, 10 and 19, are operated individually and the detection signal obtained from the operation of the first unit of probe 10 has a gradient (i.e., detection sensitivity) that is about three times as great as the gradient obtained by operating the second unit of probe 19. Because of this difference in gradient, if the A/F ratio in the fuel-lean region is detected by operating the first unit of probe 10 while the A/F ratio in the fuel-rich region is detected by operating the second unit of probe 19, a characteristic detection curve is obtained wherein the output signal changes at a substantially constant gradient over the full operating range including the fuel-rich and the fuel-lean regions, thereby ensuring constant precision of A/F ratio detection.

Figure 8:
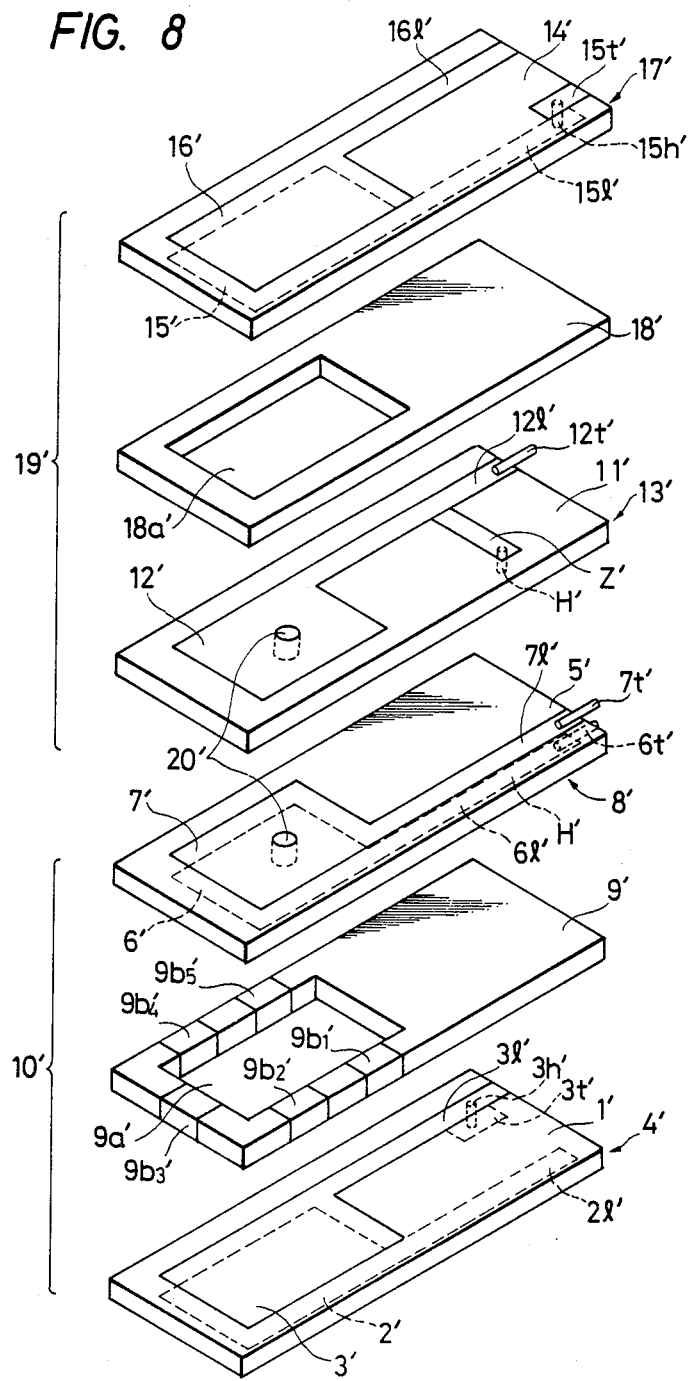
FIG. 8 is a perspective view showing another configuration of the A/F ratio sensor in an unassembled form.

In the A/F ratio sensor S according to the illustrated embodiment, the lead 7l on the porous electrode 7 serving as the internal reference oxygen source is connected to the lead 6l on the porous electrode 6 by the porous insulator Z and through-hole H so that the oxygen generated in the porous electrode 7 will leak into the gas compartment in the first unit of probe 10. In place of this arrangement, the electrical connection shown in FIG. 8 may be employed while attaining the same results; in this alternative arrangement, the lead 7l' on the porous electrode 7' is connected to the lead 12l' on the porous electrode 12' by the porous insulator Z' and the through-hole H' in such a manner that the oxygen evolved in the porous electrode 7' will leak into the gas compartment in the second unit of probe 19'. In this case, the lead 7l', porous insulator Z', through-hole H' and the lead 12l' serve as leakage resisting portions. The construction of the A/F ratio sensor shown in FIG. 8 is essentially the same as that of the sensor in accordance with the embodiment shown in FIG. 2, so that detailed explanation of the components is omitted except that they are identified by corresponding numbers suffixed with one prime (').

The foregoing explanation assumes that A/F ratio detection by the sensor S of the present invention is accomplished with the aid of the detector circuit 50 which, as shown in FIG. 7, is so designed that switching between the two units of probe for A/F ratio detection is effected automatically by means of two diodes. This type of detector circuit may be replaced by one that is designed to operate in the same manner as shown in FIG. 4 and which selectively provides A/F ratio detection in the fuel-lean or fuel-rich region by means of switches or other devices that enable selective connection between the detector circuit and the two units of probe. This type of detector circuit is indicated 60 in FIG. 9 and will produce a detection signal having the characteristics shown by the solid line in FIG. 6.

Figure 9:
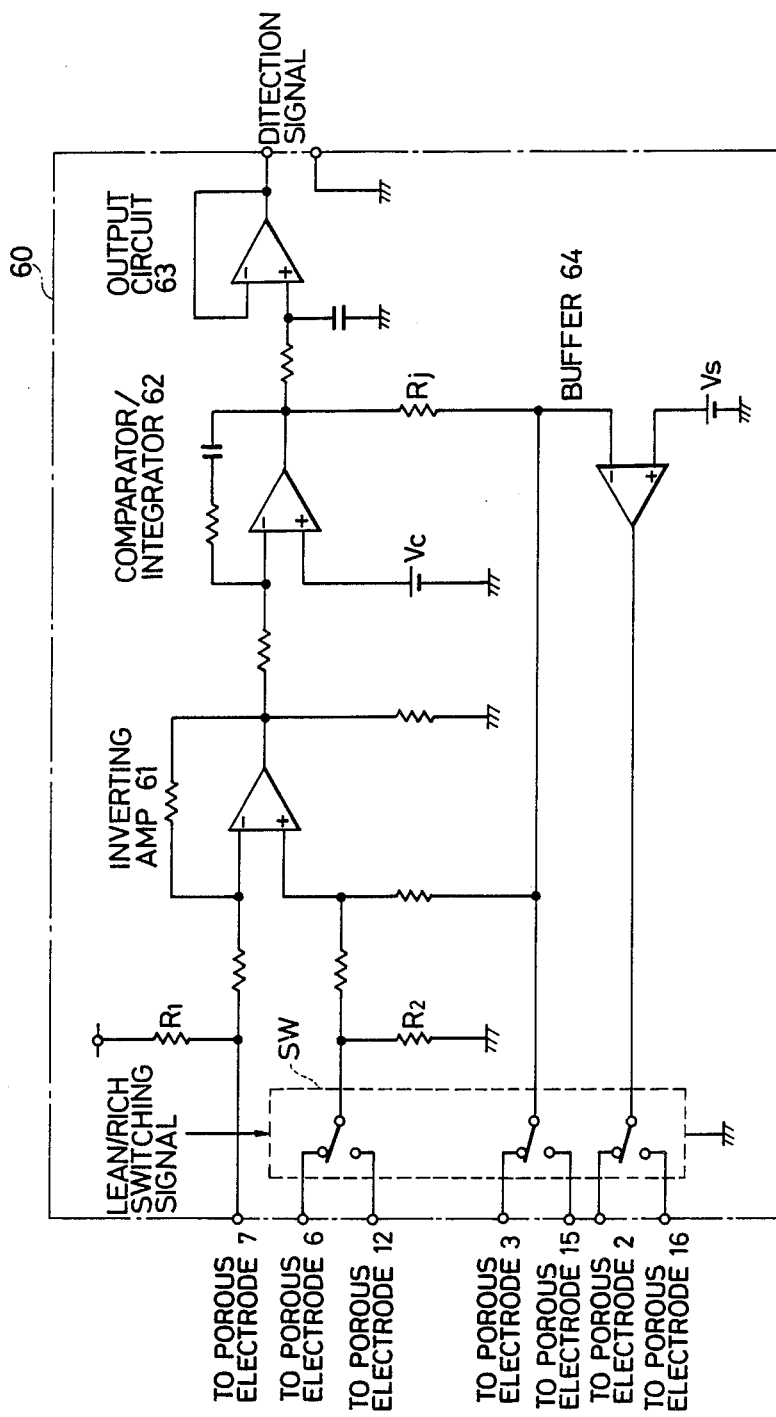
FIG. 9 is an electrical circuit diagram showing another embodiment of the A/F ratio detector circuit.

As shown in FIG. 9, the A/F ratio detector circuit 60 consists of: resistors R1 and R2 through which a predetermined voltage Vb is applied to the porous electrode 7 and which will limit the current flowing through the porous electrode 6 or 12; an inverting amplifier circuit 61 that detects the voltage developing between the porous electrode 7 and the porous electrode 6 or 12 (i.e., the voltage developing across the oxygen concentration electrochemical cell element 8 (or 13) and which amplifies the detected voltage after addition of a predetermined voltage Vs; a comparator/integrator circuit 62 that compares the voltage from the amplifier circuit 61 with a predetermined reference voltage V and outputs a control voltage having the waveform shown in FIG. 5; an output circuit 63 that produces the voltage from the circuit 62 as an output detection signal; a resistor Rj that connects the output terminal of the circuit 62 to the porous electrode 3 or 15; a buffer circuit 64 which supplies Vs to the circuit 61 and the porous electrode 3 or 15 and controls the current flowing from the porous electrode 2 to 3 or from 15 to 16 (i.e., the pump current flowing through the oxygen pump element 4 or 18) in response to the output signal from the circuit 62; and a switch unit SW that connects the detector circuit 60 with the porous electrodes 2, 3, 6 and 7 in the first unit of probe 10 when the A/F ratio to be detected is in the fuel-lean region and connects the circuit 60 to the porous electrodes 7, 12, 15 and 16 in the second unit of probe 19 when the A/F ratio is in the fuel-rich region. When the A/F ratio to be detected is in the fuel-lean region, the current flowing from the porous electrode 2 to 3 in the oxygen pump element 4 in the first unit of probe 10 is controlled by the detector circuit 60 in response to the output signal from the comparator/integrator circuit 62 such that A/F ratio detection is accomplished with the A/F ratio in the hollow portion 9a being controlled to be set in the neighborhood of the theoretical (i.e., stoichiometric) value of A/F ratio. If, on the other hand, the A/F ratio to be detected is in the fuel-rich region, the current flowing from the porous electrode 15 to 16 in the oxygen pump element 17 in the second unit of probe 19 is also controlled in response to the output signal from the circuit 62 such that A/F ratio detection is accomplished with the A/F ratio in the hollow portion 18a being controlled to be set in the neighborhood of the theoretical value of A/F ratio.

As described in the foregoing pages, the A/F ratio sensor of the present invention employs the first unit of probe to perform A/F ratio detection in the fuel-lean region, and the second unit of probe to effect A/F ratio detection in the fuel-rich region. By performing this selective operation of the sensor, the gradient of the characteristic curve for detection in the fuel-lean region can be made close to that for detection in the fuel-rich region and improved precision of detection in the fuel-lean region can be achieved. In addition, if the resistance to gas diffusion in the second diffusion limiting portion is made twice the value for the first diffusion limiting portion, a characteristic detection curve is obtained wherein detection sensitivity changes continuously over the full range of A/F ratio including the fuel-lean and the fuel-rich regions. The sensor of the present invention which provides this detection characteristic is therefore an optimum device for performing A/F ratio control.

Also, the A/F ratio sensor in accordance with the present invention has a self-compensating function for the output error caused by clogging or plugging of the diffusion limiting portion. The clogging or plugging would be gradually generated when the sensor is used for a long period of time.

Figure 10:
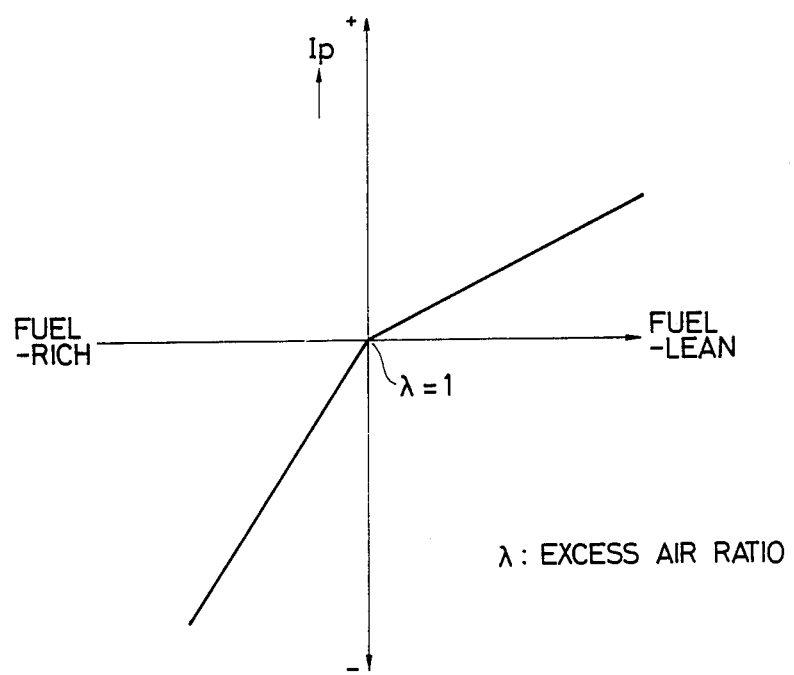
FIG. 10 is a diagram illustrating the problem of the conventional A/F ratio sensor.

In general, in the case where the sensor of this type is used in a motor vehicle, the gas diffusion limiting portion would be clogged or plugged by deposits such as metal oxide components contained in the exhaust gas and heat-resistant metal oxides in the form of fine particles, resulting in deterioration in detecting accuracy due to the change in sensor outputs representative of the A/F ratio. In contrast, in accordance with the present invention, it is possible to measure a condition of clogging irrespective of the atmosphere to be measured, since the diffusion limiting units are arranged in two series. The diffusion portions of the sensor having the characteristics shown in FIG. 10 would be clogged by the deposits, whereas the second series of the diffusion portion unit in accordance with the present invention is hardly clogged by the deposits due to the adhesion of the deposits to the unit.

More specifically, the reduction rate in current outputs of the second probe immediately after the deposits is given by:

$$Ip'_1/Ip_1 = \alpha;$$

A ratio between the current outputs that are measured by the first and second probes in the initial state, respectively, is given by:

$$Ip_1/Ip_2 = K; \text{ and}$$

A ratio between the current outputs that are measured by the first and second probes after the deposits is given by:

$$Ip'_1/Ip'_2 = K';$$

Where $Ip_1$ is the initial current output of the first probe (i.e., the oxygen pumping current when the current provided to the oxygen pumping element of the first probe is adjusted so as to keep constant the output voltage of the oxygen concentration cell element of the first probe, just after the initial use of the sensor), $Ip'_1$ is the current output of the first probe after the formation of deposits, $Ip_2$ is the initial current output of the second probe, and $Ip'_2$ is the current output of the second probe after the formation of the deposits.

Among the above-defined values of the ratios, the following relationship is established assuming that the second diffusion portion would not be clogged, while the first diffusion portion would be clogged:

$$\alpha = (K'-1)/(K-1)$$

The ratios K and K' are kept unchanged irrespective of the atmosphere to be measured. Therefore, the ratio K may be selected regardless the atmosphere in advance. The ratio K' may be determined after the formation of the deposits. Thus, the value $\alpha$ may be given to thereby correct or compensate for the outputs.

Figure 11:
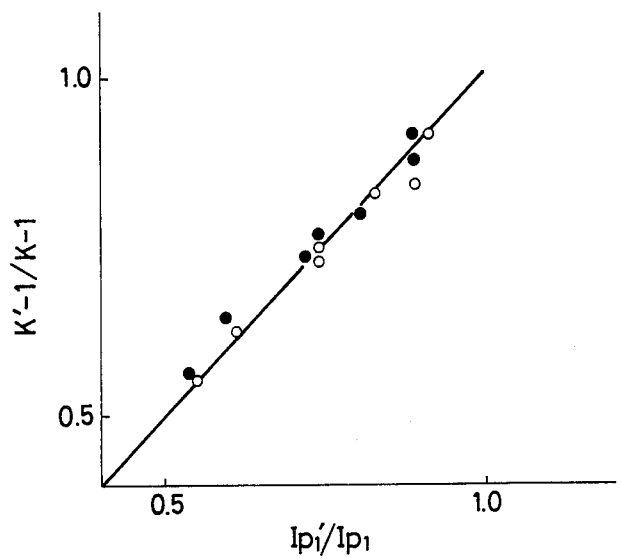
FIG. 11 is a graph showing a self-compensating function for a time-basis change due to clogging of diffusion limiting portions of the A/F ratio sensor in accordance with the present invention.

According to an experiment conducted by the present inventors, substantially constant relationship was confirmed between the current reduction rate $\alpha$ and the value of $(K'-1)/(K-1)$ over a full range from a fuel-rich region to a fuel-lean region, as shown in FIG. 11. Thus, the current output self-compensating function of the sensor in accordance with the present invention was ensured.

Also, with respect to a current output reduction rate $(\beta = Ip'_2/Ip_2)$ of the second probe, the similar relationship is established. Namely, assuming that there would be no clogging of the second probe by deposits, among the above-described ratios K and K' and the reduction rate, the following relationship is established:

$$\beta = \frac{1-(1/K')}{1-(1/K)} = \frac{K}{K'}\alpha$$

For this reason, in the same manner as $\alpha$, the reduction rate $\beta$ may be obtained, and the measurement results of the second probe may be compensated for by using the reduction rate $\beta$.

What is claimed is:

1. An air/fuel ratio sensor which employs two units of probe, each comprising:
   two sensing elements each having a pair of porous electrodes on opposite sides of an oxygen ion-conductive solid electrolyte;
   a gas compartment which is formed in contact with one porous electrode for each sensing element and which communicates with the gaseous atmosphere of interest by way of a gas diffusion limiting portion; and
   an internal reference oxygen source which is formed in contact with one sensing element on the porous electrode side which is opposite the side where said gas compartment is provided, said oxygen source communicating with the outside by way of a leakage resisting portion, the gas compartment in the first unit of probe communicating directly with the gaseous atmosphere of interest by way of a first gas diffusion limiting portion while the gas compartment in the second unit of probe communicates with the gas compartment in said first unit of probe by way of a second gas diffusion limiting portion.

2. The sensor of claim 1, wherein said internal reference oxygen source communicates with said gas compartment.

3. The sensor of claim 1, wherein a gas diffusion resistance of said second gas diffusion limiting portion is twice as large as that of said first gas diffusion limiting portion or more.

* * * * *